US 6,710,868 B2

(12) United States Patent
Guetta

(10) Patent No.: US 6,710,868 B2
(45) Date of Patent: Mar. 23, 2004

(54) OPTICAL INSPECTION SYSTEM WITH DUAL DETECTION HEADS

(75) Inventor: Avishay Guetta, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/155,487

(22) Filed: May 22, 2002

(65) Prior Publication Data

US 2003/0218741 A1 Nov. 27, 2003

(51) Int. Cl.[7] .............................................. G01N 21/00
(52) U.S. Cl. ................... 356/237.1; 356/237.2; 356/237.5; 250/201.2; 250/559.48
(58) Field of Search .................... 350/237.1–237.6, 350/394; 250/559.01, 559.06, 559.98, 559.41, 559.45, 201.2, 201.4

(56) References Cited

U.S. PATENT DOCUMENTS

| | | | | |
|---|---|---|---|---|
| 4,966,455 A | * | 10/1990 | Avni et al. ..................... 356/73 |
| 5,389,794 A | * | 2/1995 | Allen et al. ............ 250/559.48 |
| 5,898,491 A | * | 4/1999 | Ishiguro et al. ........... 356/243.4 |
| 6,084,664 A | * | 7/2000 | Matsumoto et al. ..... 356/237.4 |
| 6,104,481 A | * | 8/2000 | Sekine et al. ............. 356/237.5 |
| 6,256,093 B1 | * | 7/2001 | Ravid et al. .............. 356/237.2 |
| 6,271,916 B1 | | 8/2001 | Marxer et al. |
| 6,344,897 B2 | * | 2/2002 | Miyazaki et al. ......... 356/237.4 |
| 6,437,862 B1 | * | 8/2002 | Miyazaki et al. ......... 356/237.2 |
| 6,541,747 B1 | * | 4/2003 | Kikuchi et al. ........... 350/201.2 |

FOREIGN PATENT DOCUMENTS

WO    WO 0002037 A1    1/2000

* cited by examiner

*Primary Examiner*—Frank G. Font
*Assistant Examiner*—Sang H. Nguyen
(74) *Attorney, Agent, or Firm*—Blakley Sokoloff Taylor & Zafman LLP

(57) ABSTRACT

Apparatus for inspection of a sample includes an optical assembly made up of first and second optical heads with respective first and second levels of spatial resolution, such that the second level of spatial resolution is substantially higher than the first level. A positioning device imparts motion to at least one of the optical assembly and the sample, so as to cause the optical assembly to scan over the surface of the sample. An inspection controller processes the signal output by the first optical head to identify spots on the surface that should be inspected at the second level of spatial resolution, and then controls the second optical head so as to inspect the identified spots.

30 Claims, 3 Drawing Sheets

OPTICAL INSPECTION SYSTEM WITH DUAL DETECTION HEADS

FIELD OF THE INVENTION

The present invention relates generally to systems and methods for optical inspection, and specifically to systems for detecting and classifying defects on substrates such as semiconductor wafers.

BACKGROUND OF THE INVENTION

Optical inspection is commonly used in semiconductor device manufacturing to detect defects on the surface of a wafer, such as contaminant particles, scratches and digs. Undetected defects can cause device failures, thus reducing substantially the process yield. Therefore, careful inspection is required to verify the cleanliness and quality both of unpatterned wafers and of patterned wafers at various stages in the manufacturing process. It is desirable not only to detect the presence of defects, but also to classify them in terms of type and size, so that appropriate corrective action can be taken.

Generally speaking, the most reliable way to detect and classify defects is to capture and analyze an image of the wafer surface, but this approach is extremely time-consuming. The diameter of current semiconductor wafers typically ranges between 20 and 30 cm, over which defects as small as 0.1 $\mu$m must be detected. Therefore, to inspect and classify defects over the entire wafer, it is necessary to scan the surface at very high resolution. This approach requires costly optics, detectors and image processors, and even with high-speed image capture and processing electronics cannot reach a level of throughput sufficient to allow all wafers in process to be inspected.

An alternative approach, based on dark-field scattering detection, is proposed by Smilansky et al. in PCT Patent Publication WO 00/02037. This publication claims priority from U.S. patent application Ser. No. 09/110,870, which is assigned to the assignee of the present patent application and whose disclosure is incorporated herein by reference. Smilansky et al. described a wafer inspection system based on an optical detection head that comprises a laser and an number of light sensors, which are fed by fiberoptic light collectors arrayed around the laser. The optical head is positioned over the wafer surface, and the wafer is rotated and translated so that the laser beam scans over the surface. (Equivalently, the head could be moved over the wafer.) The sensors detect the radiation that is scattered from the surface in different angular directions simultaneously, as determined by the positions of the fiberoptics. For each pixel (defined as the area covered by the laser spot on the wafer surface at the moment the sensors are sampled), a signature is determined by the spatial pattern and intensity of the scattered radiation. The signature indicates whether there may be a defect present at the pixel and, if so, gives a general indication as to its size and type. The inventors note that their system is suitable to be integrated with a production process tool for "inline" inspection.

Another dark-field wafer inspection system is described by Marxer et al. in U.S. Pat. No. 6,271,916, whose disclosure is incorporated herein by reference. In this system, a laser beam is directed toward the wafer surface in a normal direction and scans the surface along a spiral path. An ellipsoidal mirror is used to collect the laser radiation that is scattered from the surface at angles away from the normal. Preferably, light scattered within a first range of angles is collected by one detector, while that scattered within a second range of angles is scattered by another detector. The different detector signals are used to distinguish large defects from small defects.

SUMMARY OF THE INVENTION

It is an object of some aspects of the present invention to provide an optical inspection system, particularly for semiconductor wafers, that provides both high throughput and precise classification of detected defects.

In preferred embodiments of the present invention, an inspection system comprises dual optical heads: a high-speed scanning head and a high-resolution imaging head. The high-speed head scans the entire surface of the sample under test and is used to identify the locations of suspected defects. The high-resolution head then captures images of these locations, so that the defects can be identified and classified with confidence. Preferably, the high-speed head comprises a dark-field scattering detector, such as that described by Smilansky et al. in the references cited above, while the high-resolution imaging head comprises an image sensor, such as a charge-coupled device (CCD) sensor array.

Most preferably, the two optical heads are mounted together in a single mechanical assembly, so that the relative positions of the heads are known and fixed. The assembly is advanced over the surface in such a way that each point scanned by the high-speed head subsequently enters the field of view of the high-resolution imaging head. Thus, the imaging head is able to capture high-resolution images at the discrete locations that are flagged by the high-speed head as suspected defects, while the high-speed head continues its scan. Although readout and analysis of the high-resolution images are relatively slow, they have little or no impact on the overall scanning speed or throughput of the system, since only a limited number of these images are captured and processed.

There is therefore provided, in accordance with a preferred embodiment of the present invention, apparatus for inspection of a sample, including:

an optical assembly, which includes first and second optical heads including respective first and second radiation detection devices, which are configured to capture radiation scattered from a succession of spots on a surface of the sample with respective first and second levels of spatial resolution, and to generate respective first and second signals responsive to the captured radiation, such that the second level of spatial resolution is substantially higher than the first level;

a positioning device, which is adapted to impart motion to at least one of the optical assembly and the sample, so as to cause the optical assembly to scan over the surface of the sample, whereby the first and second optical heads are positioned over the spots in the succession; and an inspection controller, which is coupled to receive and process the first and second signals and, responsive to the first signal, to identify a subset of the spots that should be inspected at the second level of spatial resolution, to control the second optical head so as to capture the scattered radiation from the spots in the subset, and to analyze the second signal to determine characteristics of the spots in the subset.

Preferably, the first and second optical heads further include respective first and second radiation sources, which are adapted to irradiate the spots in the succession, so as to generate the scattered radiation captured by the first and second radiation detection devices, respectively. Most preferably, the first and second radiation sources include laser sources.

In a preferred embodiment, the first radiation detection device includes a plurality of optical detectors, which are configured to capture the radiation scattered from the spots at different, respective angles, and the inspection controller is adapted to compare intensities of the radiation captured at the different angles so as to determine which of the spots should be included in the subset.

Preferably, the inspection controller is adapted, responsive to the first signal, to make an assessment as to a possible presence of defects in the sample at the spots in the succession, and to include the spots in the subset responsive to the assessment. Most preferably, the inspection controller is adapted to analyze the second signal so as to classify the defects at the spots in the subset.

Preferably, the second radiation detection device includes at least one image sensor, and the inspection controller is adapted to process the second signal so as to form an image of a vicinity of each of the spots in the subset, and to analyze the image in order to determine the characteristics of the spots. Most preferably, the second optical head includes a radiation source, which is adapted to direct one or more pulses of the radiation toward each of the spots in the subset while the optical assembly is scanning over the surface, which radiation is captured by the at least one image sensor to generate the second signal, so that the image of the vicinity of each of the spots is formed substantially without blur due to the motion. In a preferred embodiment, the radiation source includes a plurality of lasers, which are arranged to irradiate each of the spots at different, respective angles relative to the surface, or which are adapted to irradiate each of the spots in different, respective spectral ranges.

In an alternative embodiment, the at least one image sensor includes a plurality of image sensors, which are arranged to capture the radiation scattered from the surface at different, respective angles relative to the surface, or which are adapted to capture the radiation scattered from the surface in different, respective spectral ranges.

Preferably, the positioning device is adapted to rotate and translate the sample so that the optical assembly scans over the surface in a generally spiral pattern. Further preferably, the optical assembly is adapted to hold the first and second optical heads in substantially fixed relative positions. Most preferably, the positioning device is adapted to impart the motion so that, as the optical assembly scans over the surface, each of the spots over which the first optical head is positioned is subsequently positioned under the second optical head. Thus, the first and second heads are typically able to capture the radiation scattered from different ones of the spots in the succession and to generate the respective first and second signals responsive thereto substantially simultaneously, while the optical assembly is scanning over the surface of the sample.

There is also provided, in accordance with a preferred embodiment of the present invention, a method for inspection of a sample, including:

scanning first and second optical heads including respective first and second radiation detection devices over a surface of the sample, so as to position each of the heads over a succession of spots on the surface, the first and second heads being characterized by respective first and second levels of spatial resolution, such that the second level is substantially higher than the first level;

capturing first radiation scattered from each of the spots using the first radiation detection device at the first level of spatial resolution, and generating a first signal responsive to the captured first radiation;

receiving and processing the first signal, so as to identify a subset of the spots that should be inspected at the second level of resolution; and capturing second radiation scattered from the spots in the identified subset using the second radiation detection device at the second level of resolution, and generating a second signal responsive to the captured second radiation; and analyzing the second signal to determine characteristics of the spots in the subset.

The present invention will be more fully understood from the following detailed description of the preferred embodiments thereof, taken together with the drawings in which.

DETAILED DESCRIPTION OF PREFERRED EMBODIMENTS

Figure 1:
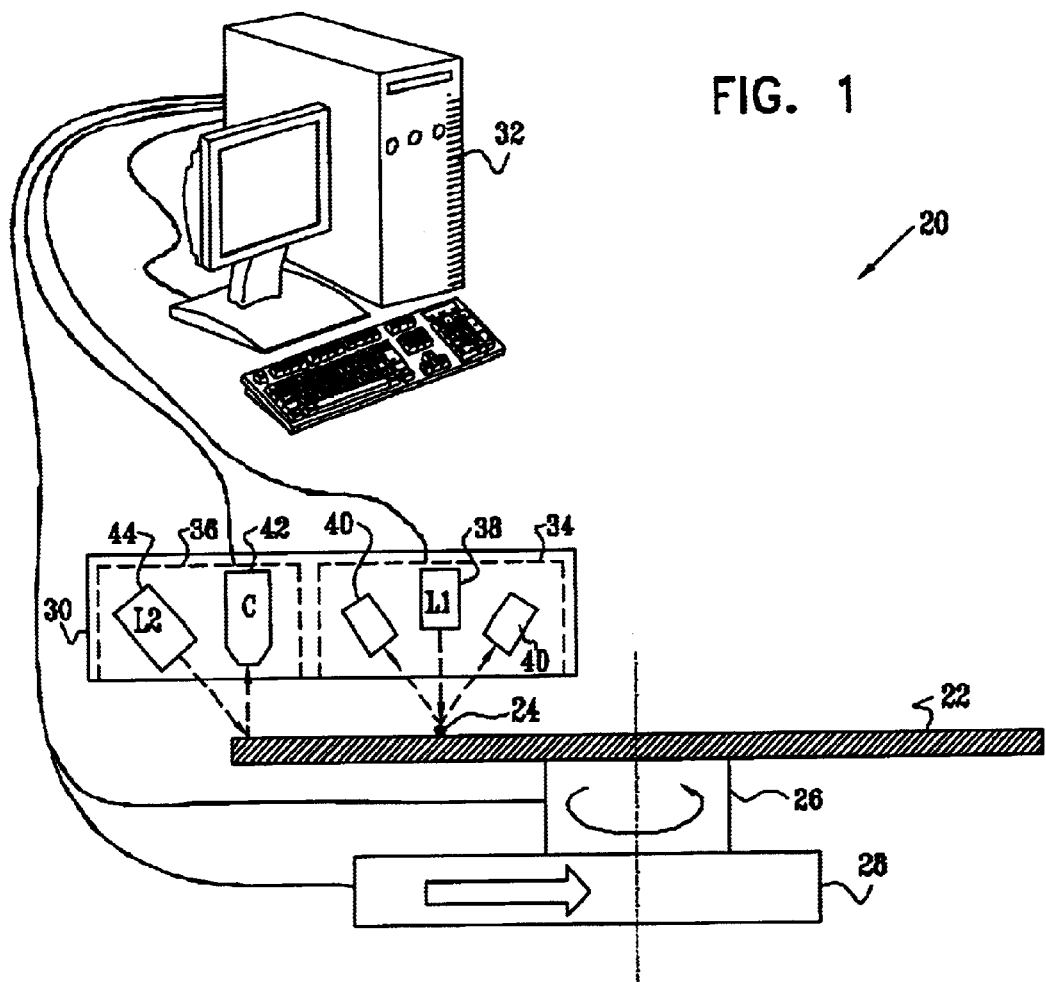
FIG. 1 is a schematic side view of an optical inspection system with dual heads, in accordance with a preferred embodiment of the present invention.

FIG. 1 is a schematic side view of a system 20 for optical inspection of a semiconductor wafer 22, in accordance with a preferred embodiment of the present invention. The wafer may be either unpatterned or patterned, in substantially any stage of its manufacturing process. The wafer is preferably held by a rotating chuck 26, as is known in the art, and is translated in a direction perpendicular to the rotation axis of the chuck by a translation stage 28 or other suitable mechanism. Preferably, the rotation and translation of wafer 22 are such as to enable an optical assembly 30 to scan the entire wafer surface, most preferably in a spiral pattern. Such arrangements are described in detail both by Smilansky et al. and by Marxer et al. in the above-cited references. Alternatively, either the translational or rotational motion, or both, may be applied to the optical assembly, rather than to the wafer. Further alternatively, the wafer and optical assembly may be configured so that the optical assembly scans over the wafer surface in a rectilinear, X-Y pattern.

Figure 2:
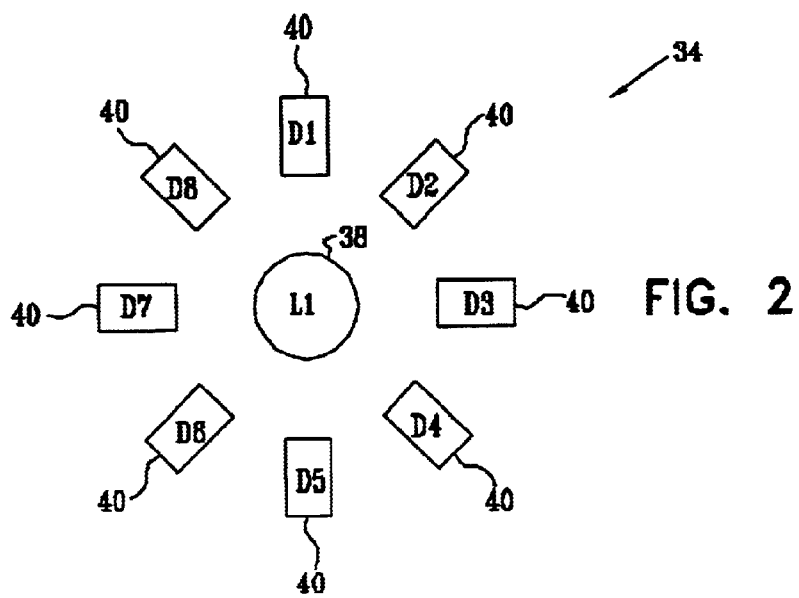
FIG. 2 is a schematic top view of a high-speed scanning head used in the system of FIG. 1, in accordance with a preferred embodiment of the present invention.

Optical assembly 30 comprises a high-speed optical head 34 and a high-resolution optical head 36, both of which communicate with an inspection controller 32. Details of heads 34 and 36 are shown in FIGS. 2 and 3, respectively, and are described with reference thereto. The purpose of head 34 is to enable controller 32 to rapidly determine the points on the surface of wafer 22 that are known or suspected to be defective. The controller then instructs head 36 to capture a high-resolution image of these points, so that the defects can be identified conclusively and classified. Note that as stage 28 translates wafer 22 to the right (in the view shown in FIG. 1), any point on the wafer scanned by head 34 will subsequently come into the field of view of head 36, enabling head 36 to capture the desired high-resolution image. Mounting heads 34 and 36 rigidly together in assembly 30 is advantageous in terms of maintaining precise, fixed relative positioning of the heads and in simplifying the mechanical scanning elements required in system 20. Alternatively, however, the two heads may be individually mounted, and their positions separately controlled.

Controller 32 typically comprises a general-purpose computer, with suitable input/output circuits and software for controlling chuck 26 and stage 28 and for receiving and processing signals from heads 34 and 36.

FIG. 2 is a schematic top view of high-speed optical head 34, in accordance with a preferred embodiment of the present invention. Head 34 comprises a laser 38, which illuminates a spot on the surface of wafer 22. Typically, the width of the spot on the surface is between 3 and 30 $\mu$m. The laser is surrounded by an array of detectors 40 (or of fiberoptic receivers, not shown in the figures, which are coupled to respective detectors.) The detectors collect radiation scattered from the laser spot on the wafer surface at different angles. Further details and alternative arrangements of the laser and detectors in head 34 are described by Smilansky et al. in the above-mentioned patent application and will not be repeated here. Other arrangements of the laser and detectors in head 34 may also be used, such as those described in the above-mentioned patent by Marxer et al. With appropriate optics, a single detector 40 may be sufficient for the purpose of identifying suspected defects for subsequent high-resolution examination.

Controller 32 analyzes the signals from detectors 40 at each spot scanned by head 34 to determine whether the signals are indicative of the presence, possible or certain, of a defect 24 at this spot. The arrangement of the detectors shown in FIG. 2 also enables the controller to make a preliminary assessment of the size and type of the defect. Controller 32 then operates high-resolution head 36 so that it captures images only of points at which there is a known or suspected defect. Optionally, the controller may apply additional decision criteria, so that head 36 images only certain types of defects, for example, or only defects whose size is estimated to be above a certain threshold, or whose scattering intensity (into certain angles or all angles) is above or below some reference level.

Figure 3A:
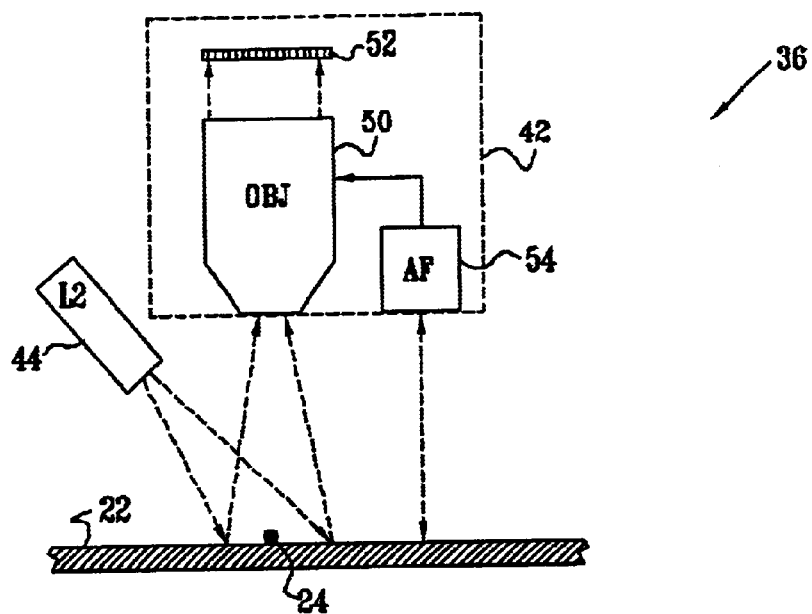
FIGS. 3A, 3B and 3C are schematic side views of high-resolution imaging head for use in the system of FIG. 1, in accordance with preferred embodiments of the present invention.

FIG. 3A is a schematic side view of high-resolution optical head 36, in accordance with a preferred embodiment of the present invention. Head 36 comprises an electronic imaging camera 42 and a laser source 44. Source 44 preferably comprises a high-intensity, pulsed laser, emitting a broad band of wavelengths, but may also include an array of laser emitters (such as diodes), each emitting a discrete wavelength. Those of skill in the art will appreciate that laser source 44 may be replaced by a flash lamp, a halogen flash lamp and the like.

Most preferably, laser 44 comprises a white-light laser. The pulsed operation of the laser enables camera 42 to capture an image without blur, even wile wafer 22 is rotating rapidly. The broadband illumination is useful in enabling camera 42 to capture a color image of wafer 22, which is known to provide additional useful diagnostic information, beyond what can be offered by a monochrome image. Alternatively, however, a narrowband laser source and monochrome camera may also be used.

Camera 42 comprises an objective lens 50 and an image sensor 52, such as a CCD array sensor. Sensor 52 thus captures an image of the surface of wafer 22 with substantially higher resolution that the 3–30 $\mu$m resolution achieved by high-speed head 34. For color imaging with high resolution, the camera preferably comprises two or three sensor arrays, operating in different wavelength bands, as is known in the art.

Camera 42 may be a Dalstar or Piranha CCD camera of Dalsa technology Co., having an objective magnification of 5–100×, pixel size of 0.2–2 Micron amd field of fiew of 0.2–2 mm, but other cameras having other characteristics may be used.

Because wafer 22 tends to bow and bend while held by chuck 26, the distance from the wafer surface to objective 50 typically varies substantially as optical assembly 30 scans over the wafer. Objective 50 preferably has sufficient depth of field to accommodate the entire range of distances that can occur between the wafer surface and the camera. Alternatively, an autofocus device 54, such as an acoustic or optical sensor, measures the distance from the wafer surface to the camera and adjusts the focus of objective 50 accordingly. If necessary, should controller 32 determine that an image captured by camera 42 was out of focus, it can instruct chuck 26 and stage 28 to move high-resolution head 36 back over that point so as to capture a new image that is in focus.

Figure 3B:
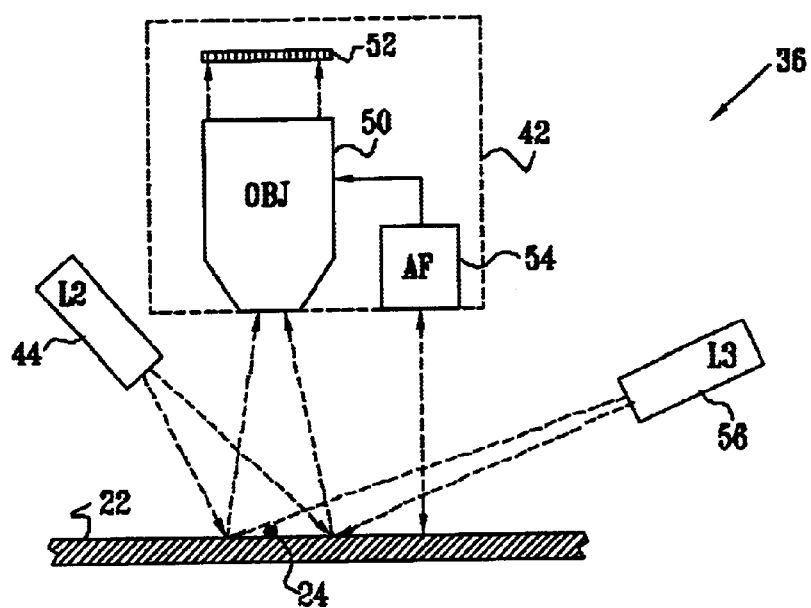
Figure 3C:
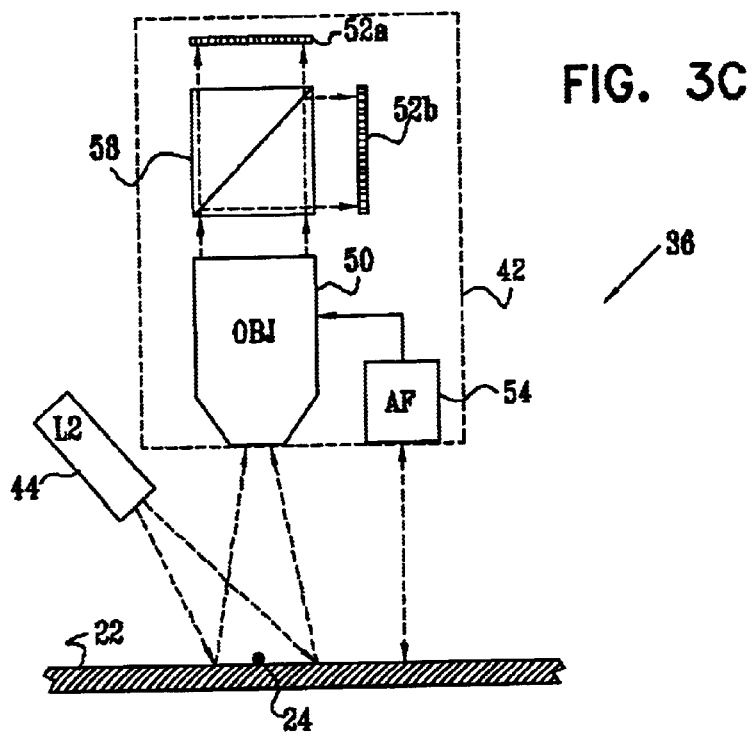

FIGS. 3B and 3C are schematic side views of high-resolution optical head 36, in accordance with alternative embodiments of the present invention. In FIG. 3B, head 36 comprises multiple lasers 44 and 56. These lasers may be of the same type, or of different types. Different type lasers may be used, for example, to illuminate the wafer surface with different colors, thus enabling high-resolution multi-spectral imaging of the surface. A similar benefit may be achieved by using multiple sensors 52a and 52b, as shown in FIG. 3C. The sensors preferably receive light from the wafer surface via a dichroic beamsplitter 58, so that each sensor receives a different spectral range. Although for the sake of simplicity, only two lasers 44 and 56 and only two sensors 52a and 52b are shown in these figures, three or more lasers and/or sensors could be used in like manner.

Alternatively or additionally, lasers 44 and 56 may be arranged, as shown in FIG. 3B, to illuminate the wafer surface at different angles. The lasers can be fired in sequence so that camera 42 captures light scattered from defect 24 in a number of different angular ranges. This angular scattering pattern may be useful in visualizing and classifying very small defects. It is also possible to arrange multiple sensors at different angles in order to perform this sort of multi-angle detection.

Figure 4:
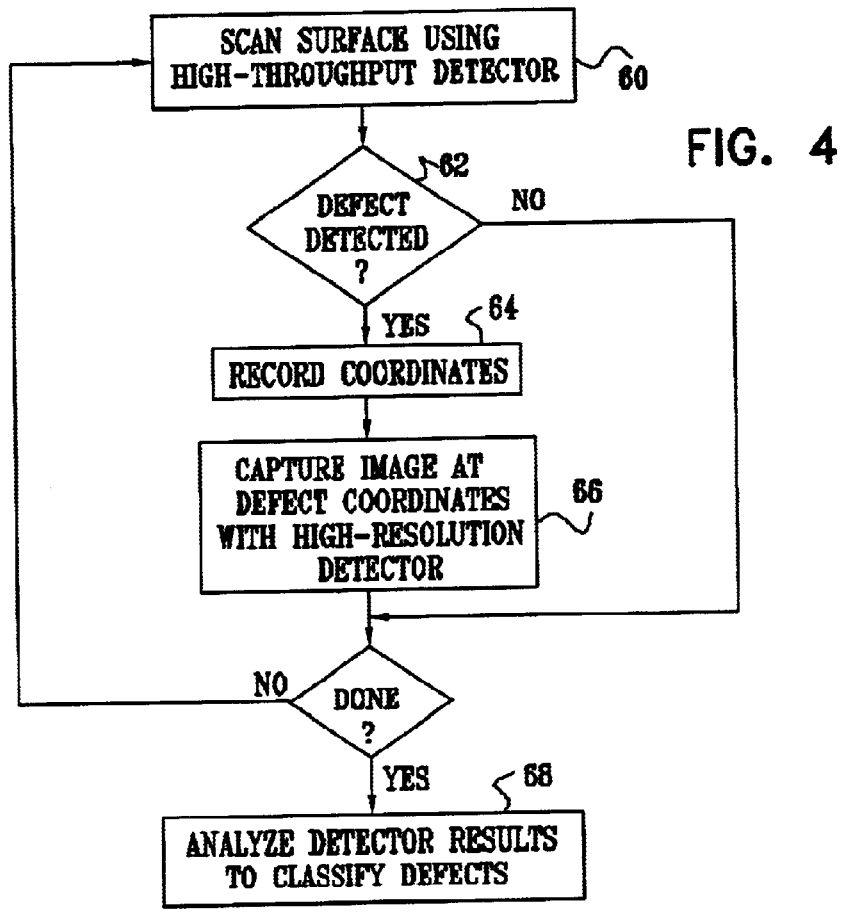
FIG. 4 is a flow chart that schematically illustrates a method for optical inspection of a surface, in accordance with a preferred embodiment of the present invention.

FIG. 4 is a flow chart that schematically illustrates a method for detecting and classifying defects on the surface of wafer 22 using system 20, in accordance with a preferred embodiment of the present invention. As noted above, the entire surface of the wafer, or at least a sizable portion of the surface, is scanned using high-speed head 34, at a scanning step 60. From each point on the surface, there is an expected level and angular distribution of scattered radiation, depending on whether the wafer is patterned or unpatterned, and also depending, for patterned wafers, on the nature and composition of the pattern. Significant deviations from the expected level and distribution of radiation are noted by controller 32, at a defect detection step 62. The controller records the translational and rotational coordinates of each definite or likely defect that it finds, at a coordinate recording step 64.

When high-resolution head 36 subsequently passes over each of the coordinate points recorded at step 64, laser 44 is fired, and camera 42 captures a high-resolution image of the vicinity of the coordinate point, at an imaging step 66. As noted above, controller 32 may be programmed to apply selection criteria, so that the high-resolution head captures images only at certain defect points at which further detailed analysis is believed to be required. The image data are read out of camera 42 to controller 32 during the time that the high-resolution head is scanning toward the next defect coordinate point. Therefore, the relatively slow speed and processing of the camera readout does not substantially affect the throughput of system 20.

Controller 32 analyzes the images from camera 42, along with the scattering data collected at step 60, in order to classify all the defects found on the wafer surface, at a defect classification step 68. As noted above, if the controller determines that one or more of the images were out of focus or otherwise inadequate, it can scan head 36 back over the defect point and capture a new image. When the entire scan is completed, controller 32 preferably outputs a map of the wafer, showing the points at which defects were detected and their classification as to type and size. This information can be used by an operator of system 20 in deciding on corrective action to be taken.

Although the preferred embodiments described above refer specifically to inspection of semiconductor wafers, the principles of the present invention may similarly be applied to inspection of photomasks and other items used in the semiconductor manufacturing process, as well as to other areas of automated optical inspection. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for inspection of a sample, comprising:

an optical assembly, which comprises first and second optical heads comprising respective first and second radiation detection devices, which are configured to capture radiation scattered from a succession of spots on a surface of the sample with respective first and second levels of spatial resolution, and to generate respective first and second signals responsive to the captured radiation, such that the second level of spatial resolution is substantially higher than the first level;

a positioning device, which is adapted to impart motion to at least one of the optical assembly and the sample, so as to cause the optical assembly to scan over the surface of the sample, whereby the first and second optical heads are positioned over the spots in the succession; and an inspection controller, coupled to receive and process the first and second signals and, responsive to the first signal, configured to identify a subset of the spots that should be inspected at the second level of spatial resolution, to control the second optical head so as to capture the scattered radiation from the spots in the subset, and to analyze the second signal to determine characteristics of the spots in the subset.

2. Apparatus according to claim 1, wherein the first and second optical heads further comprise respective first and second radiation sources, which are adapted to irradiate the spots in the succession, so as to generate the scattered radiation captured by the first and second radiation detection devices, respectively.

3. Apparatus according to claim 2, wherein the first and second radiation sources comprise laser sources.

4. Apparatus according to claim 1, wherein the first radiation detection device comprises a plurality of optical detectors, which are configured to capture the radiation scattered from the spots at different, respective angles, and wherein the inspection controller is adapted to compare intensities of the radiation captured at the different angles so as to determine which of the spots should be included in the subset.

5. Apparatus according to claim 1, wherein the inspection controller is adapted, responsive to the first signal, to make an assessment as to a possible presence of defects in the sample at the spots in the succession, and to include the spots in the subset responsive to the assessment.

6. Apparatus according to claim 5, wherein the inspection controller is adapted to analyze the second signal so as to classify the defects at the spots in the subset.

7. Apparatus according to claim 1, wherein the second radiation detection device comprises at least one image sensor, and wherein the inspection controller is adapted to process the second signal so as to form an image of a vicinity of each of the spots in the subset, and to analyze the image in order to determine the characteristics of the spots.

8. Apparatus according to claim 7, wherein the second optical head comprises a radiation source, which is adapted to direct one or more pulses of the radiation toward each of the spots in the subset while the optical assembly is scanning over the surface, which radiation is captured by the at least one image sensor to generate the second signal, so that the image of the vicinity of each of the spots is formed substantially without blur due to the motion.

9. Apparatus according to claim 8, wherein the radiation source comprises a plurality of lasers, which are arranged to irradiate each of the spots at different, respective angles relative to the surface.

10. Apparatus according to claim 8, wherein the radiation source comprises a plurality of lasers, which are adapted to irradiate each of the spots in different, respective spectral ranges.

11. Apparatus according to claim 7, wherein the at least one image sensor comprises a plurality of image sensors, which are arranged to capture the radiation scattered from the surface at different, respective angles relative to the surface.

12. Apparatus according to claim 7, wherein the at least one image sensor comprises a plurality of image sensors, which are adapted to capture the radiation scattered from the surface in different, respective spectral ranges.

13. Apparatus according to claim 1, wherein the positioning device is adapted to rotate and translate the sample so that the optical assembly scans over the surface in a generally spiral pattern.

14. Apparatus according to claim 1, wherein the optical assembly is adapted to hold the first and second optical heads in substantially fixed relative positions.

15. Apparatus according to claim 14, wherein the positioning device is adapted to impart the motion so that, as the optical assembly scans over the surface, each of the spots over which the first optical head is positioned is subsequently positioned under the second optical head.

16. Apparatus according to claim 15, wherein the first and second heads are adapted to capture the radiation scattered from different ones of the spots in the succession and to generate the respective first and second signals responsive thereto substantially simultaneously, while the optical assembly is scanning over the surface of the sample.

17. A method for inspection of a sample, comprising:

scanning first and second optical heads comprising respective first and second radiation detection devices over a surface of the sample, so as to position each of the heads over a succession of spots on the surface, the first and second heads being characterized by respective first and second levels of spatial resolution, such that the second level is substantially higher than the first level;

capturing first radiation scattered from each of the spots using the first radiation detection device at the first level of spatial resolution, and generating a first signal responsive to the captured first radiation;

receiving and processing the first signal, so as to identify a subset of the spots that should be inspected at the second level of resolution; and capturing second radiation scattered from the spots in the identified subset using the second radiation detection device at the second level of resolution, and generating a second signal responsive to the captured second radiation; and analyzing the second signal to determine characteristics of the spots in the subset.

18. A method according to claim 13, wherein the first and second optical heads further comprises respective first and second radiation sources, and wherein capturing the first and second radiation comprises irradiating the spots in the succession using the first and second radiation sources, respectively, so as to generate the scattered radiation captured by the first and second radiation detection devices.

19. A method according to claim 18, wherein the first and second radiation sources comprise laser sources.

20. A method according to claim 17, wherein capturing the first radiation comprises capturing the first radiation scattered from the spots at a plurality of different angles, and wherein processing the first signal comprises comparing intensities of the radiation captured at the different angles so as to determine which of the spots should be included in the subset.

21. A method according to claim 17, wherein processing the first signal comprises making an assessment, responsive to the first signal, as to a possible presence of defects in the sample at the spots in the succession, and including the spots in the subset responsive to the assessment.

22. A method according to claim 21, wherein analyzing the second signal comprises classifying the defects at the spots in the subset.

23. A method according to claim 17, wherein capturing the second radiation comprises forming an image of a vicinity of each of the spots in the subset, and wherein analyzing the second signal comprises processing the image in order to determine the characteristics of the spots.

24. A method according to claim 23, wherein forming the image comprises directing pulsed radiation toward each of the spots in the subset while scanning the first and second optical heads over the surface, and wherein forming the image comprises capturing the pulsed radiation to generate the second signal, so that the image of the vicinity of each of the spots is formed substantially without blur due to the scanning.

25. A method according to claim 17, wherein capturing the second radiation comprises capturing the second radiation scattered from the surface at a plurality of different scattering angles.

26. A method according to claim 17, wherein capturing the second radiation comprises capturing the second radiation scattered from the surface in a plurality of different spectral ranges.

27. A method according to claim 17, wherein scanning the first and second optical heads comprises rotating and translating the sample so that the optical heads scan over the surface in a generally spiral pattern.

28. A method according to claim 17, wherein scanning the first and second optical heads comprises holding the first and second optical heads in substantially fixed relative positions during the scanning.

29. A method according to claim 28, wherein the positioning device is adapted to impart the motion so that, as the optical assembly scans over the surface, each of the spots over which the first optical head is positioned is subsequently positioned under the second optical head.

30. A method according to claim 29, wherein capturing the first and second radiation comprises capturing the second radiation from one of the spots in the subset substantially simultaneously with capturing the first radiation from a subsequent one of the spots in the succession, while scanning the first and second optical heads over the surface of the sample.

* * * * *